United States Patent [19]
Wolf

[11] Patent Number: 5,714,442
[45] Date of Patent: Feb. 3, 1998

[54] COMPOUNDS WITH (BENZO) TRIAZOLE RADICALS

[75] Inventor: Jean-Pierre Wolf, Courtaman, Switzerland

[73] Assignee: Ciba Speciality Chemicals Corporation, Tarrytown, N.Y.

[21] Appl. No.: 637,190

[22] Filed: Apr. 8, 1996

[30] Foreign Application Priority Data

Apr. 11, 1995 [CH] Switzerland ............... 1070/95

[51] Int. Cl.$^6$ ........................................... C10M 133/38
[52] U.S. Cl. .................... 508/279; 508/281; 548/260; 548/266.4; 106/287.2
[58] Field of Search .................... 508/279, 280, 508/281; 548/260, 266.4; 106/287.2

[56] References Cited

U.S. PATENT DOCUMENTS

| | | |
|---|---|---|
| 3,531,414 | 9/1970 | Randall et al. . |
| 4,153,565 | 5/1979 | Braid et al. . |
| 4,177,155 | 12/1979 | Popplewell et al. . |
| 4,636,359 | 1/1987 | Penninger ............... 422/13 |
| 4,701,273 | 10/1987 | Brady et al. . |
| 4,734,209 | 3/1988 | Phillips et al. . |
| 5,076,948 | 12/1991 | O'Neil et al. . |

FOREIGN PATENT DOCUMENTS

| | | |
|---|---|---|
| 0006710 | 1/1980 | European Pat. Off. . |
| 0160620 | 11/1985 | European Pat. Off. . |
| 0365476 | 4/1990 | European Pat. Off. . |
| 0385951 | 9/1990 | European Pat. Off. . |
| 1521762 | 9/1969 | Germany . |
| 2601719 | 7/1976 | Germany . |
| 8501964 | 5/1985 | WIPO . |

OTHER PUBLICATIONS

Journal Organic Chemistry, 54 (1989), pp. 6022–6029, Katritzky et al.
J. Chem. Soc. Perkin Trans. I, 1989, pp. 639–642.
J. Heterocyclic Chem., 27, (1990), pp. 1543–1547.
J. Chem. Soc. Perkin Trans. I, 1987, pp. 791–797.
Chem. Abst. vol. 93, No. 25, 239321n, 1980.

*Primary Examiner*—Prince Willis, Jr.
*Assistant Examiner*—Cephia D. Toomer
*Attorney, Agent, or Firm*—David R. Crichton; Victoria M. Malia

[57] ABSTRACT

A description is given of compounds of the formula I, and mixtures thereof,

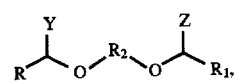

(I), in which Y and Z independently of one another are a radical of the formula

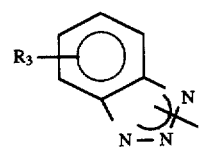

or

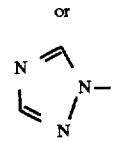

(III)

R and $R_1$ independently of one another are hydrogen, $C_1$–$C_{12}$alkyl, $C_5$–$C_8$cycloalkyl, $C_1$–$C_4$alkyl-substituted $C_5$–$C_8$cycloalkyl, phenyl or $C_1$–$C_4$alkyl-substituted phenyl.

$R_2$ is $C_2$–$C_{20}$alkylene, $C_5$–$C_8$cycloalkylene, a radical of the formula

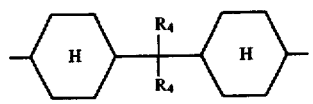

The compounds/mixtures are particularly suitable as metal deactivators for use in lubricants.

16 Claims, No Drawings

COMPOUNDS WITH (BENZO) TRIAZOLE RADICALS

The invention relates to novel compounds which are suitable in particular as metal deactivators and corrosion inhibitors and have triazole and/or benzotriazole groups, to mixtures of these compounds, to compositions comprising these compounds or mixtures thereof, and to their preparation and use.

It is known that copper ions catalyse autoxidation and the formation of peroxide radicals in organic materials. This is also true of the oxidative degradation of lubricants (cf. Ullmann's Encyclopaedia of Industrial Chemistry, Vol. A3, p. 104). By adding benzotriazole or benzotriazole derivatives, usually together with antioxidants, it is possible to slow down considerably the decomposition of the lubricant by copper.

Examples of the compounds currently used in industry are those of the type

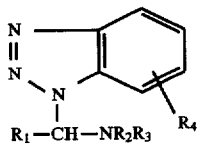

in which, for example, R, is hydrogen, $R_2$ and $R_3$ are 2-ethylhexyl or hydroxyethyl and $R_4$ is hydrogen or methyl (see. e.g. U.S. Pat. No. 4,683,071 and U.S. Pat. No. 4,701,273).

U.S. Pat. No. 5,076,948 describes N-triazole compounds having alkoxy groups. N-Benzotriazole compounds having alkoxy groups are known, furthermore, from U.S. Pat. Nos. 4,153,565 and U.S. Pat. No. 5,032,300.

Katritzky et al. describe compounds containing two benzotriazole radicals which are attached via nitrogen [A. R. Katritzky et al., J. Chem Soc. Perkin Trans. 1987, 791; 1990, 1717;

J. Heterocyclic Chem. 27, 1543 (1990)].

There continues to be a need for active substances having metal-deactivating and/or corrosion-preventing properties.

It has now been found that the compounds described in more detail below, containing two (benzo)triazole radicals, possess outstanding metal-deactivating and corrosion-preventing properties.

The invention therefore provides compounds of the formula I

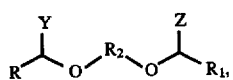

in which

Y and Z independently of one another are a radical of the formula

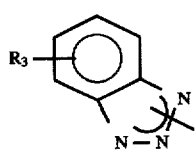

or

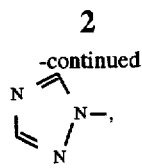

R and $R_1$ independently of one another are hydrogen, $C_1-C_{12}$alkyl, $C_5-C_8$cycloalkyl, $C_1-C_4$alkyl substituted $C_5-C_8$cycloalkyl, phenyl or $C_1-C_4$alkyl-substituted phenyl, $R_2$ is $C_2-C_{20}$alkylene, $C_5-C_8$cycloalkylene, a radical of the formula

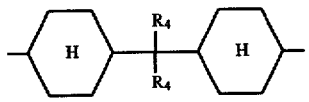

or $(C_nH_{2n}O)_mC_nH_{2n}$ in which n is 2, 3 or 4 and m is 1 to 20, $R_3$ is hydrogen or $C_1-C_4$alkyl, and $R_4$ is hydrogen or methyl, and mixtures of such compounds.

The invention also relates in particular to mixtures of the compounds of the formula I just described in which the radicals Y and Z are different with compounds of the formula I in which the radicals Y and Z are identical.

Advantageous compounds or compound mixtures of the formula I are those in which

R and $R_1$ are hydrogen, $C_1-C_9$alkyl or phenyl, $R_2$ is $C_2-C_{15}$alkylene, $C_5-C_8$cycloalkylene, a radical of the formula

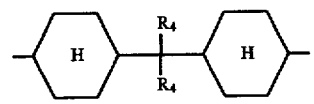

or $—(C_nH_{2n}O)_mC_nH_{2n}—$, in which n is 2, 3 or 4 and m is 1 to 10, and $R_3$ is hydrogen or methyl.

In the compounds of the formula 1, R and $R_1$ are preferably identical.

Preference is given, furthermore, to compounds of the formula I in which R and $R_1$ are hydrogen or $C_1-C_6$alkyl, $R_2$ is $C_2-C_{12}$alkylene, cyclohexylene or a radical of the formula

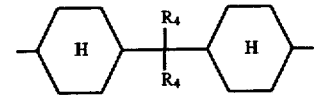

or $(C_nH_{2n}O)_mC_nH_{2n}$ in which n is 2, 3 or 4 and m is 1 to 10, and $R_3$ is hydrogen or methyl.

In the compounds just described, with particular preference, R and $R_1$ are hydrogen or $C_1-C_6$alkyl and $R_2$ is $C_2-C_8$alkylene or cyclohexylene or a radical of the formula

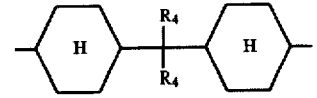

$C_1-C_{12}$alkyl radicals can be straight-chain or branched and depending on the number of carbon atoms specified are for example m. ethyl, ethyl, propyl, isopropyl, n-butyl, isobutyl, t-butyl, pentyl, isopentyl, hexyl, heptyl, octyl, 2-ethylhexyl, nonyl, decyl, undecyl, dodecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, or 1-methylundecyl.

$R_3$ as alkyl preferably has 1–4 carbon atoms and in particular is methyl.

$C_5$–$C_8$cycloalkyl is for example cyclopentyl, cyclohexyl or cyclooctyl; cycloalkyl radicals having 5 or 6 carbon atoms are preferred, especially cyclohexyl.

$C_5$–$C_8$cycloalkylene can for example be cyclohexylene, cyclopentylene or cyclooctylene. It is preferably cyclohexylene.

$C_1$–$C_4$alkyl substituted phenyl is preferably substituted with methyl or ethyl and, in particular, is mesityl, xylyl or tolyl.

The invention also provides a process for the preparation of compounds of the formula I and mixtures thereof, in which process triazole of the formula

(IV)

or a benzotriazole of the formula

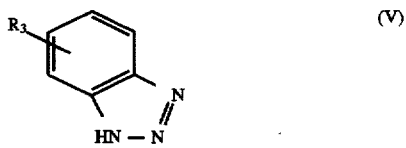

(V)

or mixtures thereof (i) is or are reacted with aldehydes $R_1CHO$ or $RCHO$ or mixtures of such aldehydes and diols $HO—R_2—OH$, in which the radicals R, $R_1$, $R_2$ and $R_3$ are as defined initially, or (ii), if $R_1$ and R are methyl and $R_2$ and $R_3$ are as defined initially, reaction is carried out with divinyl ethers of the formula $H_2C=CH—O—R_2—O—CH=CH_2$.

In this context it is possible to employ any desired mixtures of compounds of the formulae IV and V provided mixtures of these compounds are used to start with. In such mixtures, the molar ratio IV:V is preferably in the range from 1:99 to 99:1, in particular from 1:9 to 9:1 and, very especially, from 1:4 to 4:1.

The invention additionally provides the products or product mixtures obtainable by the above process.

The individual species in the mixtures of different compounds of the formula I can either be obtained by using pure, unmixed starting materials in pure form (cf. Examples 2, 6, 13 below), or can be isolated from the mixtures by conventional physical separation methods, for example chromatography.

Since it is therefore possible, for the preparation of the compound's of the formula I and mixtures thereof, to employ triazole

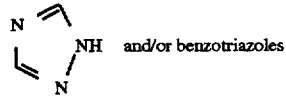 and/or benzotriazoles (IV)

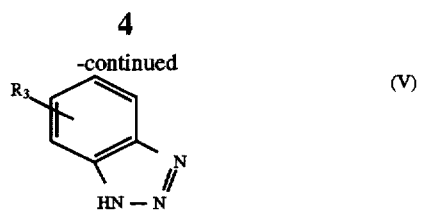

in any desired ratios, the composition of the mixtures according to the invention depends on the ratio in which the starting materials IV and V are employed. The reactivity of benzotriazole derivatives and triazole in the reactions which are possible for the preparation is substantially the same. The reaction therefore produces mixtures of compounds of the formula I with identical and different radicals Y and Z, whose composition depends substantially on the concentration of the reactants and has a substantially statistical distribution of the reaction products.

The unspecified site of the free bond in formula II

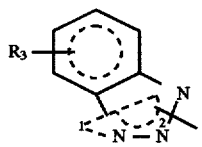

is intended to indicate that in each case substitution may occur in position 1 or 2 of the benzotriazole, since the benzotriazole exists in mesomeric resonance structures.

Examples of suitable methods for the preparation of the compounds of the formula I are the two methods explained below and illustrated in detail in the Examples, which methods are familiar in organic chemistry (cf. A. R. Katritzky et al., J. Chem Soc. Perkin Trans. 1987, 791; 1990, 1717; J. Heterocyclic. Chem. 27, 1543 (1990); J. Chem. Soc. Perkin Trans. 1989, 639). The benzotriazole and/or triazole can be reacted with an equimolar quantity of aldehyde and with half the molar quantity of a diol of the formula $HO—R_2—OH$, for instance with catalysis by an acid—p-toluenesulfonic acid, for example. Alternatively, the (benzo)triazole can be reacted directly with half the molar quantity of a divinyl ether of the formula $H_2C=CH—O—R_2—O—CH=CH_2$ (VI)—advantageously likewise with acid catalysis. In this case, compounds of the formula I are obtained in which R and $R_1$ are methyl (see equation below).

The reactions take place, for example, in accordance with the following equation:

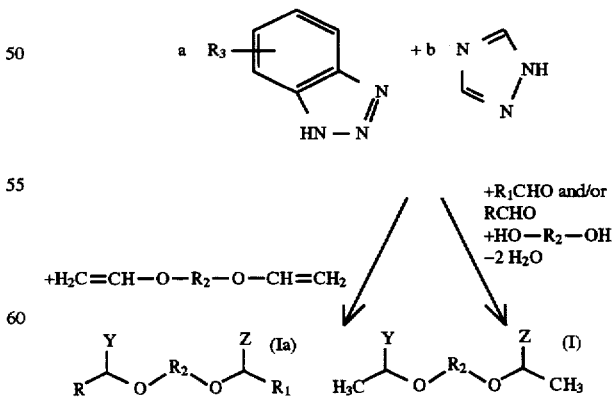

In this equation the radicals Y, Z, R and $R_1$ to $R_3$ have the definitions given initially, and a and b adopt values from 0 to 2, the sum of a and b being 2.

The condensation may take place in apolar organic solvents with catalysis by an acid such as, expediently, para-toluenesulfonic acid.

The compounds can also be prepared in alcohols or alcohol/water mixtures, for example in ethanol, methanol or mixtures thereof with water. Under these conditions, it is also possible to omit the acid catalyst.

As mentioned above, the products can be substituted in position 1 or 2 of the benzotriazole system (1- or 2-benzotriazolyl compounds). Separation of any isomers is not necessary, but can be done by customary methods, for example chromatography. In practice, it is preferred to employ the mixtures obtained directly from the reaction.

The starting materials employed are commercially obtainable or can be prepared by known methods. It should be mentioned that, when employing methylbenzotriazole, it is preferable to use a mixture of 4- and 5-methylbenzotriazole.

The compounds according to the invention are outstandingly suitable as metal deactivators and antioxidants for organic materials, especially those materials which come into contact with metals or comprise metal ions as impurities. For lubricants, there is also a distinct antiwear activity. The invention therefore also provides compositions comprising a1) a lubricant, a metalworking fluid or a hydraulic fluid or a2) a coating composition, especially a paint or varnish, and b) at least one compound of the formula I, in which context the compounds of the formula I and mixtures thereof mentioned above as preferred lead to preferred compositions.

The compounds of the formula I contribute to the prevention of oxidation and decomposition processes, in particular by binding copper ions and thus deactivating them. The invention therefore also provides for the use of compounds of the formula I as additives in lubricants, hydraulic fluids, metalworking fluids and coatings compositions, especially as metal deactivators and corrosion inhibitors.

The lubricants, metalworking fluids and hydraulic fluids concerned are based, for example, on mineral oils, synthetic oils or mixtures thereof. The lubricants are familiar to the person skilled in the art and are described in the relevant technical literature, for example in Dieter Klamann, "Schmierstoffe und verwandte Produkte" [Lubricants and related products] (Verlag Chemie, Weinheim, 1982), in Schewe-Kobek, "Das Schmiermittel-Taschenbuch" [The Lubricants Handbook] (Dr. Alfred Hüthig-Verlag, Heidelberg, 1974) and in "Ullmanns Enzyklopädie technischen Chemie" [Ullmann's Encyclopaedia of Industrial Chemistry], Vol.13, pages 85–94 (Verlag Chemie, Weinheim, 1977).

The lubricants are, in particular, oils and fats based, for example, on a mineral oil. Oils are preferred.

A further group of lubricants which may be employed are vegetable or animal oils, fats, tallows and waxes or mixtures thereof with one another, or mixtures with the mineral or synthetic oils mentioned. Examples of vegetable and animal oils, fats, tallows and waxes are palm kernel oil, palm oil, olive oil, colza oil, rapeseed oil, linseed oil, groundnut oil, soya bean oil, cottonseed oil, sunflower oil, pumpkinseed oil, coconut oil, maize oil, castor oil, walnut oil and mixtures thereof, fish oils, tallows from slaughtered animals, such as beef tallow, neat's-foot and bone oil, and the modified, epoxidized and sulfoxidized forms thereof, for example epoxidized soya bean oil.

The mineral oils are based in particular on hydrocarbon compounds.

The examples of synthetic lubricants comprise lubricants based on aliphatic or aromatic carboxylic esters, polymeric esters, polyalkylene oxides, phosphoric esters, poly-α-olefins or silicones, a diester of a dibasic acid with a monohydric alcohol, for example dioctyl sebacate or dinonyl adipate, a triester of trimethylolpropane with a monobasic acid or of a mixture of such acids, for example trimethylolpropane tripelargonate, trimethylol propane tricaprylate or mixtures thereof, a tetraester of pentaerythrite with a monobasic acid or a mixture of such acids, for example pentaerythrite tetracaprylate, or a complex ester of monobasic and dibasic acids with polyhydric alcohols, for example a complex ester of trimethylolpropane with caprylic and sebacic acid or of a mixture thereof. Particularly suitable lubricants, in addition to mineral oils, are for example poly-α-olefins, ester-based lubricants, phosphates, glycols, polyglycols and polyalkylene glycols, and mixtures thereof with water.

Metalworking fluids and hydraulic fluids can be prepared on the bases of the same substances as described above for the lubricants. Frequently, they also comprise emulsions of such substances in water or other liquids.

Lubricant compositions according to the invention are used, for example, in combustion engines, for example in motor vehicles with are fitted, for example, with engines of the Otto spark-ignition, diesel, two-stroke, Wankel or orbital type.

The compounds of the formula I are readily soluble in lubricants, metalworking fluids and hydraulic fluids and are therefore particularly suitable as additives to lubricants, metalworking fluids and hydraulic fluids.

The compounds of the formula I and/or mixtures thereof can be admixed to the lubricants in a manner known per se. The compounds are, for example, readily soluble in oils. It is also possible to prepare a so-called masterbatch which can be diluted to application concentration levels with the appropriate lubricant in accordance with use. In such cases, concentrations of more then 10% by weight are also possible.

The compounds according to the invention as described above can be present, for example, in quantities of from 0.01 to 10% by weight, expediently in quantities of from 0.01 to 5% by weight, preferably in a quantity of from 0.01 to 3% by weight and, with very particular preference, in a quantity of from 0.01 to 1.5% by weight, based on the composition, in the lubricant, metalworking fluid or hydraulic fluid.

In addition to the compounds according to the invention, the lubricants, metalworking fluids and hydraulic fluids can comprise other customary additives, examples being further antioxidants, metal deactivators, rust inhibitors, viscosity index improvers, pour-point depressants, dispersants/surfactants, and extreme-pressure and antiwear additives.

Examples of these are:

Examples of phenolic antioxidants

1. Alkylated monophenols, for example 2,6-di-tert-butyl-4-methylphenol, 2-tert-butyl-4,6-dimethylphenol, 2,6'di-tert-butyl-4-ethylphenol, 2,6-di-tert-butyl-4-n-butylphenol, 2,6-di-tertbutyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methyl-undec-1'-yl)phenol, 2,4-dimethyl-6-(1 '-methyl-heptadec-1'-yl)phenol, 2,4-dimethyl-6-(1'-methyltridec-1'-yl)phenol and mixtures thereof.

2. Alkylthiomethylphenols, for example 2,4-di-octylthiomethyl-6-tert-butylphenol, 2,4-dioctylthiomethyl-6-methylphenol, 2,4-dioctylthiomethyl-6-ethylphenol, 2,6-didodecyl thiomethyl-4-nonylphenol.

3- Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octa decyloxyphenol, 2,6-di-tert-butyl-hydroquinone, 2,5-di-tert-butyl-4-hydroxyanisole, 3,5-di-tert-butyl-4-hydroxyanisole, 3,5-ditert-butyl-4-hydroxyphenyl stearate, bis(3,5-di-tert-butyl-4-hydroxyphenyl) adipate.

4. Tocopherols, for example α-tocopherol, β-tocopherol, γ-tocopherol, δ-tocopherol and mixtures thereof (Vitamin E).

5. Hydroxylated thiodiphenyl ethers, for example 2,2'-thiobis(6tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis (3-tert-butyl-5- methyl-2-hydrexybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methyl-benzyl)-6-tert-butyl-4-methyl-phenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

7. O-, N- and S-Benzyl compounds, for example 3,5,3', 5'-tetra-tert-butyl-4,4'-dihydroxydibenzyl ether, octadecyl 4-hydroxy-3,5-di-methylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis-(3,5-di-tert-butyl-4-hydroxybenzyl) sulfide, iso octyl 3,5-di-tert-butyl-4-hydroxybenzylmercaptoacetate.

8. Hydroxybenzylated malonates, for example dioctadecyl 2,2-bis(3,5-di-tert-butyl-2-hydroxybenzyl) malonate, di-octadecyl 2-(3-tert-butyl-4-hydroxy-5-methylbenzyl)malonate, di-dodecyl mercaptoethyl 2,2-bis(3,5-di-tert-butyl-4-hydroxybenzyl)malonate, di-[4-(1,1,3,3tetramethylbutyl)phenyl] 2,2-bis(3,5-di-tert-butyl-4-hydroxybenzyl)malonate.

9. Aromatic hydroxybenzyl compounds, for example 1,3, 5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris (3,5-di-tert-butyl-4-hydroxybenzyl)phenol.

10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris (4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3, 5-triazine, 1,3,5-tris(3,5-dicyclohexyl-4-hydroxybenzyl) isocyanurate.

11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of monoethyl 3,5-di-tert-butyl-4-hydroxybenzylphosphonate.

12. Acylaminophenols, for example 4-hydroxylauranilide, 4-hydroxystearanilide, octyl N-(3,5-di-tert-butyl-4-hydroxyphenyl)carbamate.

13. Esters of β-(3,5-di-tert-butyl-4-hydroxyphenyl) propionic acid with mono- or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis (hydroxyethyl)oxalamide, 3-thiaundecanol, 3-thiapentadecanol, tri methylhexanediol, trimethylolpropane, 4-hydroxymethyl-1-phospha-2,6, 7-trioxabicyclo[2.2.2]octane.

14. Esters of β-(5-tert-butyl-4-hydroxy-3-methylphenyl) propionic acid with mono- or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis (hydroxyethyl)oxalamide, 3-thiaundecanol, 3-thiapentadecanol, tri methylhexanediol, trimethylolprbpane, 4-hydroxymethyl-1-phospha-2,6, 7-trioxabicyclo[2.2.2]octane.

15. Esters of β-(3,5-dicyclohexyl-4-hydroxyphenyl) propionic acid with mono- or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis (hydroxyethyl)oxalamide, 3-thiaundecanol, 3-thiapentadecanol, tri methylhexanediol, trimethylolpropane, 4-hydroxymethyl-1-phospha-2,6, 7-trioxabicyclo [2.2.2]octane.

16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thio-diethylene glycol, di ethylene glycol, triethylene glycol, pentaerythritol, tris(hydroxyethyl) isocyanurate, N,N'-bis (hydroxyethyl)oxalamide, 3-thiaundecanol, 3-thiapentadecanol, trimethylhexanediol, trimethylolpropane, 4-hydroxymethyl-1-phospha-2,6, 7-trioxabicyclo[2.2.2]octane.

17. Amides of β-(3,5-di-tert-butyl-4-hydroxyphenyl) propionic acid, for example N,N'-bis(3,5-di-tert-butyl-4-hydroxyphenylpropionyl)hexamethylendiamine, N,N'-bis(3,5-di-tert-butyl-4-hydroxyphenylpropionyl) trimethylendiamine, N,N'-bis(3,5-di-tert-butyl-4-hydroxyphenylpropionyl)hydrazine.

Examples of amine-type antioxidants:.

N,N'-di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine N-(1-methyl-heptyl)-N'-phenyl-p-phenylenediamine, N-cyclohexyl-N'-phenyl-p-phenylenediamine, 4-(p-toluenesulfonamido) diphenylamine, N,N'-dimethyl-N,N'-di-sec-butyl-p-phenylenediamine, diphenylamine, N-allyldiphenylamine, 4-iso propoxy-diphenylamine, N-phenyl-1-naphthylamine, N-phenyl-2-naphthylamine, octylated diphenylamine, for example p,p'-di-tert-octyldiphenylamine, 4-n-butylaminophenol, 4-butyryl amino-phenol, 4-nonanoylamino-phenol, 4-dodecanoylamino-phenol, 4-octa decanoylamino-phenol, di-(4-methoxyphenyl)amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-[(2-methyl-phenyl)-amino]ethane, 1,2-di- (phenylamino) -propane, (o-tolyl)biguanide, di-[4-(1',3'-dimethyl-butyl)-phenyl]amine, tert-octylated N-phenyl-1-naphthylamine, a mixture of mono- and dialkylated tert-butyl/tert-octyl diphenylamines, a mixture of mono- and dialkylated isopropyl/isohex yl-diphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethyl-piperid-4-yl)hexamethylendiamine, bis(2,2,6,6-tetramethylpiperid-4-yl) sebacate, 2,2,6,6-tetramethylpiperidin-4-one, 2,2,6,6-tetramethylpiperidin-4-ol.

Examples of further antioxidants:

Aliphatic or aromatic phosphites, esters of thiodipropionic acid or of thiodiacetic acid, or salts of dithiocarbarnic acid or dithiophosphoric acid, 2,2,12,12-tetra methyl-5,9-dihydroxy-3,7,11-trithiatridecane and 2,2,15,15-tetra methyl-5,12-dihydroxy-3,7,10,14-tetrathiahexadecane.

Examples of metal deactivators, for example for copper, are:

a) Benzotriazoles and derivatives thereof, for example 4- or 5-alkylbenzotriazoles (e.g. tolutriazole), and derivatives thereof, 4,5,6,7-tetrahydrobenzotriazole, 5,5'-methylenebisbenzotriazole; Man nich bases of benzotriazole or tolutriazole such as 1-[di(2-ethylhexyl)amino methyl] tolutriazole and 1-[di(2-ethylhexyl)aminomethyl] benzotriazole; alkoxyalkyl benzotriazoles, such as 1-(nonyloxymethyl)benzotriazole, 1-(1-butoxyethyl) benzotriazole and 1-(1-cyclo hexyloxybutyl)tolutriazole.

b) 1,2,4-Triazoles and derivatives thereof, for example 3-alkyl (or aryl)- 1,2,4-triazoles, Mannich bases of 1,2,4-triazoles, such as 1-[di(2-ethylhexyl)amino methyl]-1,2,4-triazoles; alkoxyalkyl-1,2,4-triazoles, such as 1-(1-butoxyethyl)-1,2,4-triazoles; acylated 3-amino-1,2,4-triazoles.

c) Imidazole derivatives, for example 4,4'-methylenebis (2-undecyl)-5-methylimidazole, bis[(N-methyl)imidazol-2-yl]carbinol octyl ether.

d) Sulfur-containing heterocyclic compounds, for example 2-mercaptobenzothiazole, 2,5-di mercapto-1, 3,4-thiadiazole and derivatives thereof; 3,5-bis[di(2-ethylhexyl)amino-methyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, dioles or hydroxycarboxylic acids, partial amides of alkyl- and alkenylsuccinic acids, 4-no nylphenoxyacetic acid, alkoxy- and alkoxyethoxycarboxylic acids, such as dodecy loxyacetio acid, dodecyloxy(ethoxy)acetic acid and the amine salts thereof, and also N-oleoylsarcosine, sorbitol monooleate, lead naphthenate, alkenylsuccinic anhydrides, for example dodecenylsuccinic anhydride, 2-carboxymethyl-1-dodecyl-3-methylglycerol and amine salts thereof.

b) Nitrogen-containing compounds, for example:

I. Primary, secondary or tertiary aliphatic or cycloaliphatic amines and amine salts of organic and inorganic acids, for example oil-soluble alkyl ammonium carboxylates, and also 1-[N,N-bis(2-hydroxyethyl)amino]-3-(4-nonylphenoxy)propan-2-ol.

II. Heterocyclic compounds, for example:

Substituted imidazolines and oxazolines, 2-heptadecenyl-1-(2-hydroxyethyl)imidazoline.

c) Phosphorus-containing compounds, for example:

Amine salts of phosphoric partial esters or phosphonic partial esters, zinc di alkyldithiophosphates.

d) Sulfur-containing compounds, for example:

Barium dinonylnaphthalenesulfonates, calcium petroleumsulfonates, alkylthio-substituted aliphatic carboxylic acids, esters of aliphatic 2-sulfocarboxylic acids and salts thereof.

e) Glycerol derivatives, for example:

Glycerol monooleate, 1-(alkylphenoxy)-3-(2-hydroxyethyl)glycerols, 1-(alkyl phenoxy)-3-(2,3-dihydroxypropyl)glycerols, 2-carboxyalkyl-1,3-dialkylglycerols.

Examples of viscosity index improvers are:

Polyacrylates, polymethacrylates, vinylpyrrolidonemethacrylate copolymers, polyvinyl-pyrrolidones, polybutenes, olefin copolymers, styrene-acrylate copolymers, polyethers.

Examples of pour-point depressants are:

Polymethacrylate, alkylated naphthalene derivatives.

Examples of dispersants/surfactants are:

Polybutenylsuccinamides or -imides, polybutenylphosphonic acid derivatives, basic magnesium, calcium and barium sulfonates and phenolates.

Examples of antiwear additives are:

Compounds comprising sulfur and/or phosphorus and/or halogen, such as sulfurized olefins and vegetable oils, zinc dialkyldithiophosphates, alkylated triphenyl phosphates, tritolyl phosphate, tricresyl phosphate, chlorinated paraffins, alkyl and aryl di- and tri-sulfides, amine salts of mono- and dialkyl phosphates, amine salts of methyl phos phonic acid, diethanolaminomethyltolyltriazole, di(2-ethylhexyl) aminomethyltolyltriazole, derivatives of 2,5-dimercapto-1, 3,4-thiadiazole, ethyl 3-[(bis-isopropyl oxyphosphinothioyl)thio]-propionate, triphenyl thiophosphate (triphenylphosphorothioate), tris(alkyl phenyl) phosphorothioates and mixtures thereof (e.g. tris(isononyl phenyl) phosphorothioate), diphenylmonononylphenyl phosphorothioate, isobutylphenyldiphenyl phosphorothioate, the dodecylamine salt of 3-hydroxy-1,3-thiaphosphetane-3-oxide, tri thiophosphoric acid 5,5,5-tris [2-isooctylacetate], derivatives of 2-mercaptobenzthiazole, such as 1-[N,N-bis(2 ethylhexyl)aminomethyl]-2-mercapto-1H-1,3-benzthiazole, 5-ethoxycarbonyloctyl dithiocarbamate.

The compounds according to the invention are particularly effective together with phenolic and/or amine-type antioxidants.

Coating compositions generally consist of binders and additives with or without colouring components.

Suitable binders are in principal all those which are customary in the art, for example those as described in Ullmann's Encyclopaedia of Industrial Chemistry, 5th. ed., Vol. A18, pp. 368–426, VCH, Weinheim 1991. The binder is generally a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

The binder may be a cold-curable or hot-curable binder, the addition of a curing catalyst possibly being advantageous. Examples of suitable catalysts which accelerate the curing of the binder are described in Ullmann's Encyclopaedia of Industrial Chemistry, Vol. A18, p. 469, VCH Verlagsgesellschaft, Weinheim 1991.

Preferred coating compositions are those in which the film-forming binder comprises epoxy resins, polyurethane resins, polyester resins, acrylic resins and copolymer resins thereof, poylvinyl resins, phenolic resins, alkyd resins or mixtures of such resins.

The compounds of the formula I can be present in the coating compositions in proportions of from 0.001 to 10%, preferably from 0.1 to 5%.

Where the compositions according to the invention are coating compositions, or paints or varnishes, then these may likewise comprise further customary components from the groups, for example, consisting of dyes, pigments, fillers, flow control agents, adhesion promoters, curing catalysts, light stabilizers and antioxidants.

Preferred compounds according to the invention, as described above, lead to preferred compositions.

The present invention also provides for the use of compounds or compound mixtures of the formula I as additives in lubricants, hydraulic fluids and metalworking fluids, or coating compositions, and a method of improving the service properties of lubricants, metalworking fluids or hydraulic fluids or coating compositions, which comprises adding compounds or compound mixtures of the formula I to these lubricants, fluids or compositions.

The examples which follow illustrate the invention in more detail but without limiting it. Unless otherwise specified, parts and percentages are by weight. All operations are carried out under nitrogen. If the products already begin to crystallise while the reaction solution is being cooled, they are isolated by filtration and not subjected to any further purification.

EXAMPLES

Preparation Examples (In the tables and in the remainder of the description, Me is methyl and the group

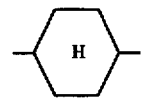

is cyclohexylene).

Method 1

0.2 mol of (benzo)triazole, 0.2 mol of aldehyde, 0.1 mol of diol (c.f. Table 1 ) and 0.2 g of p-toluenesulfonic acid in 200 ml of cyclohexane are charged to a 4-neck sulfonating flask (flat-bottomed reaction vessel) with mechanical stirrer, Dean-Stark water separator, thermometer and nitrogen inlet.

The reaction solution is heated at reflux until the theoretical quantity of 0.2 mol of water has separated out.

The reaction solution is cooled to room temperature and washed three times with 100 ml of aqueous 5% $Na_2CO_3$ solution and with twice 100 ml of water and is dried over $MgSO_4$, and the solvent is removed by distillation on a rotary evaporator. Finally, the residue is dried at 60° C. under a high vacuum for 2 hours.

TABLE 1

| | Examples according to method 1 | | | | | |
|---|---|---|---|---|---|---|
| Ex. No. | Precursors | Yield | | Elemental analysis | | |
| 1 | Me [structure] 1:1 H₃C~~O, HO~~OH | 28% orange oil | found: | C: 64.2 | H: 8.3 | N: 17.9 |

TABLE 1-continued

Examples according to method 1

| Ex. No. | Precursors | Yield | Elemental analysis | | |
|---|---|---|---|---|---|
| 2 | benzotriazole, butyraldehyde, 1,4-cyclohexanedimethanol | 98% yellow oil | calc.: found: | C: 68.5  H: 7.8<br>C: 69.1  H: 8.4 | N: 17.1<br>N: 14.8 |
| 3 | methylbenzotriazole, butyraldehyde, 1,4-cyclohexanedimethanol | 100% orange oil | calc.: found: | C: 69.5  H: 8.2<br>C: 70.1  H: 8.8 | N: 16.2<br>N: 14.0 |
| 4 | benzotriazole, butyraldehyde, 2,2-bis(4-hydroxycyclohexyl)propane | 99% yellow-orange oil | calc.: found: | C: 71.4  H: 8.6<br>C: 72.6  H: 9.5 | N: 14.3<br>N: 12.1 |
| 5 | methylbenzotriazole, butyraldehyde, 2,2-bis(4-hydroxycyclohexyl)propane | 99% yellow resin | calc.: found: | C: 72.3  H: 8.9<br>C: 73.4  H: 9.6 | N: 13.7<br>N: 11.4 |
| 6 | benzotriazole, butyraldehyde, 1,4-cyclohexanediol | 98% orange oil | calc.: found: | C: 67.5  H: 7.4<br>C: 67.8  H: 7.8 | N: 18.2<br>N: 16.7 |
| 7 | methylbenzotriazole, butyraldehyde, 1,4-cyclohexanediol | 98% orange oil | calc.: found: | C: 68.5  H: 7.8<br>C: 69.3  H: 8.4 | N: 17.1<br>N: 14.8 |
| 8 | methylbenzotriazole, butyraldehyde, Polyethylene glycol 300 | 88% orange oil | calc.: found: | C: 62.2  H: 8.0<br>C: 63.5  H: 8.5 | N: 12.8<br>N: 10.8 |

TABLE 1-continued

Examples according to method 1

| Ex. No. | Precursors | Yield | Elemental analysis | | |
|---|---|---|---|---|---|
| 9 | 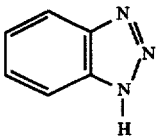<br> O, Polyethylene glycol 400 | 83%<br>yellow-orange oil | calc.:<br>found: | C: 60.9  H: 8.2<br>C: 62.7  H: 8.7 | N: 10.7<br>N: 9.8 |

Method 2

0.2 Mol of triazole, 0.1 mol of divinyl ether and 0.2 g of p-toluenesulfonic acid in 100 ml of solvent (cf. Table 2) are charged to a 4-neck sulfonation flask with mechanical stirrer, reflux condenser, thermometer and nitrogen inlet.

The reaction solution is boiled at reflux until the precursors have disappeared (checked by thin-layer chromatography).

The reaction solution is cooled to room temperature, washed three times with 100 ml of aqueous 5% $Na_2CO_3$ solution and twice with 100 ml of water and dried over $MgSO_4$, and the solvent is removed by distillation on a rotary evaporator. Finally, the residue is dried at 60° C., under a high vacuum for 2 hours.

TABLE 2

Examples according to Method 2

| Exp. No. | Precursors | Solvent | Yield | Elemental analysis | | |
|---|---|---|---|---|---|---|
| 10 | 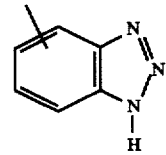 | Toluene | 86%<br>brown oil | calc:<br>found: | C: 59.3  H: 7.0<br>C: 58.6  H: 7.2 | N: 24.4<br>N: 23.5 |
| 11 | 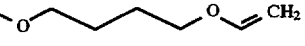 | Cyclohexane | 91%<br>brown Resin | calc:<br>found: | C: 64.7  H: 6.9<br>C: 64.8  H: 7.0 | N: 20.6<br>N: 20.4 |

Method 3

0.2 Mol of (benzo)triazole, 0.1 mol of divinyl ether and 0.2 g of p-toluenesulfonic acid in 100 ml of solvent (cf. Table 3) are charged to a 4-neck sulfonation flask with mechanical stirrer, reflux condenser, thermometer and nitrogen inlet.

The reaction solution is boiled at reflux until the precursors have disappeared (checked by thin-layer chromatography). The reaction solution is cooled to room temperature, 5 g of powdered CaO and a little $MgSO_4$ are added, stirring is carried out for 10 minutes and the suspension is filtered. The filtrate is concentrated on a rotary evaporator and the product is dried at 60° C. under a high vacuum for 2 hours.

TABLE 3

Examples according to Method 3

| Ex. No. | Precursors | Solvent | Yield | Elemental analysis | | |
|---|---|---|---|---|---|---|
| 12 | Me-benzotriazole / triazole / H₂C=CH-O-(CH₂)₄-O-CH=CH₂  1:1 | A | 85% orange-red oil | Calc: C: 59.3  found: C: 58.8 | H: 7.0  H: 7.1 | N: 24.4  N: 23.7 |
| 13 | triazole / H₂C=CH-O-(CH₂)₄-O-CH=CH₂ | A | 38% orange oil | Calc: C: 51.4  found: C: 51.4 | H: 7.2  H: 7.3 | N: 29.0  N: 29.9 |
| 14 | Me-benzotriazole / triazole / H₂C=CH-O-(CH₂)₄-O-CH=CH₂  1.6:0.4 | B | 90% red-brown resin | calc: C: 62.7  found: C: 62.4 | H: 7.0  H: 7.0 | N: 22.0  N: 22.5 |
| 15 | Me-benzotriazole / triazole / H₂C=CH-O-(CH₂)₄-O-CH=CH₂  1.2:0.8 | B | 94% red-brown resin | calc: C: 60.5  found: C: 60.4 | H: 7.0  H: 7.0 | N: 23.5  N: 23.9 |
| 16 | Me-benzotriazole / triazole / H₂C=CH-O-(CH₂)₄-O-CH=CH₂  0.4:1.6 | B | 93% red oil | calc: C: 55.0  found: C: 54.8 | H: 7.1  H: 7.1 | N: 27.5  N: 27.9 |

Solv. (solvent):
A = Carbon tetrachloride
B = Toluene

Method 4

0.2 Mol of (benzo)triazole, 0.2 mol of butyraldehyde, 0.1 mol of 1,4-bis(hydroxymethyl)cyclohexane and 0.2 g of p-toluenesulfonic acid in a mixture of 100 ml of cyclohexane and 100 ml of toluene are heated at reflux in a 4-neck sulfonation flask with mechanical stirrer, Dean-Stark water separator, thermometer and nitrogen inlet.

After the theoretical quantity of 0.2 mol of water has separated off, the mixture is cooled to room temperature. 5 g of CaO and a little MgSO₄ are added, stirring is carried out for 10 minutes, and the suspension is filtered. The filtrate is concentrated on a rotary evaporator and the product is dried at 60° C. under a high vacuum for 2 hours.

TABLE 4

Examples according to Method 4

| Ex. No. | Precursors | Yield | Elemental analysis | | | |
|---|---|---|---|---|---|---|
| 17 | Me-benzotriazole structure with 1.6:0.4 ratio, H₃C-CH=CH-CHO, and HO-cyclohexyl-CH₂OH | 96% orange resin | calc: found: | C: 68.2<br>C: 68.2 | H: 8.3<br>H: 8.3 | N: 17.0<br>N: 17.0 |
| 18 | Me-benzotriazole structure with 1.2:0.8 ratio, H₃C-CH=CH-CHO, and HO-cyclohexyl-CH₂OH | 96% orange resin | calc: found: | C: 66.8<br>C: 66.7 | H: 8.4<br>H: 8.4 | N: 18.0<br>N: 17.3 |
| 19 | Me-benzotriazole structure with 0.4:1.6 ratio, H₃C-CH=CH-CHO, and HO-cyclohexyl-CH₂OH | 97% orange oil | calc: found: | C: 63.5<br>C: 63.3 | H: 8.6<br>H: 8.7 | N: 20.2<br>N: 18.7 |

Use examples

Example A1: Copper corrosion test (modified from ASTM D-130)

0.05% by weight of the compound to be tested is dissolved in a turbine oil of viscosity 29.7 $mm^2s^{-1}$ at 40° C. and 5.05 $mm^2s^{-1}$ at 100° C. (sulfur content 0.22%). In addition, 50 ppm of elemental sulfur are added.

A copper plate (60×10×1 mm) polished with silicon carbide is immersed completely in the oil solution and left there at 100° C. for 3 hours. The copper plate is then removed from the oil and rinsed with petroleum ether. It is subsequently assessed in accordance with the ASTM D 130 Copper Strip Corrosion Standard Chart (cf. Table 5). There are four levels of evaluation:

1—no tarnishing

2—moderate tarnishing

3—severe tarnishing

4—corrosion;

within the numerical groups 1 to 4, additional precision subdivision is undertaken on the basis of the clouding on the samples. In this qualitative assessment, A to E, the rating A is before B, B is before C, etc. The table shows in each case values for two panels (parallel determination).

TABLE 5

Copper corrosion test

| Compound from Example No. | Assessment |
|---|---|
| — | 3B/4A |
| 10 | 1A/1A |
| 13 | 1A/1A |
| 1 | 1A/1B |
| 14 | 1A/1A |
| 15 | 1A/1A |
| 16 | 1A/1A |

Example A2: Rotary Bomb Oxidation Test (RBOT), ASTM D 2272

0.05% by weight of the compound to be tested are dissolved in a turbine oil (viscosity 29.7 $mm^2s^{-1}$ at 40° C. and 5.05 $mm^2s^{-1}$ at 100° C., sulfur content 0.22%). Further components are 0.15% of a phenolic antioxidant[1], 0.05% of an amine-type antioxidant[2] and 0.07% of a corrosion inhibitor[3] (cf. Table below). 50 ml of the mixture thus obtained are added together with 5 ml of water to the test vessel, which contains a copper coil as catalyst. The vessel is charged with oxygen up to a pressure of 620 kPa, and is then sealed and rotated in a hot bath at 150° C. A measurement is made of the time over which the oxygen pressure falls by 172 kPa.

TABLE 6

| Compound from Example No. | Rotary Bomb Oxidation Test (RBOT) Time [min] |
|---|---|
| — | 278 |
| 10 | 830 |
| 13 | 1048 |
| 1 | 751 |
| 14 | 1039 |
| 15 | 1084 |
| 16 | 1155 |

[1])Mixture of tert-butylated phenols, obtainable as Irganox ™ 140
[2])Mixture of diphenylamine compounds, commercially available as Irganox ™-57, cf. US-5,073,278, col. 2, line 50
[3])Hitec ™ 536,
$H_{23}C_{12}-CH(COOH)-CH_2-CO-NH-CH_2-CH_2-NH-CH_2-CH_2-N\underset{C_{17}H_{33}}{\overset{\frown}{\phantom{N}}}N$

What is claimed is:

1. A compound of the formula I

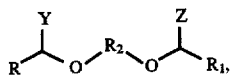

in which

Y and Z independently of one another are a radical of the formula

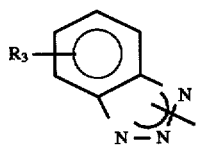

or

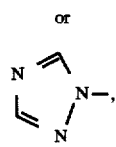

R and $R_1$ independently of one another are hydrogen, $C_1$–$C_{12}$alkyl, $C_5$–$C_8$cycloalkyl, $C_1$–$C_4$alkyl-substituted $C_5$–$C_8$cycloalkyl, phenyl or $C_1$–$C_4$alkyl-substituted phenyl.

$R_2$ is $C_2$–$C_{20}$alkylene, $C_5$–$C_8$cycloalkylene, a radical of the formula

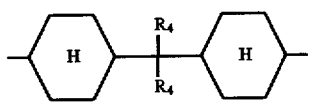

or $(C_nH_{2n}O)_mC_nH_{2n}$ in which n is 2, 3 or 4 and m is 1 to 20, $R_3$ is hydrogen or $C_1$–$C_4$alkyl, and $R_4$ is hydrogen or methyl.

2. A compound according to claim 1, wherein R and $R_1$ are identical.

3. A compound according to claim 1, wherein

R and $R_1$ are hydrogen, $C_1$–$C_9$alkyl or phenyl, $R_2$ is $C_2$–$C_{15}$alkylene, $C_5$–$C_8$cycloalkylene, a radical of the formula

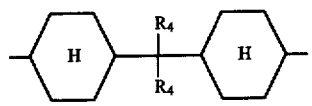

or $-(C_nH_{2n}O)_mC_nH_{2n}-$, in which n is 2, 3 or 4 and m is 1 to 10, and $R_3$ is hydrogen or methyl.

4. A compound according to claim 1, wherein R and $R_1$ are hydrogen or $C_1$–$C_6$alkyl.

$R_2$ is $C_2$–$C_{12}$ alkylene, cyclohexylene or a radical of the formula

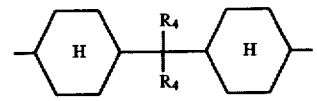

or $(C_nH_{2n}O)_mC_nH_{2n}$ in which n is 2, 3 or 4 and m is 1 to 10, and $R_3$ is hydrogen or methyl.

5. A compound or mixture according to claim 4, wherein $R_2$ is $C_2$–$C_8$alkylene or cyclohexylene or a radical of the formula

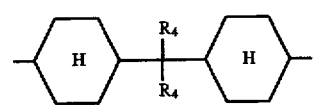

6. A process for the preparation of compounds of the formula I defined in claim 1 and mixtures thereof, which comprises reacting the compound of the formula

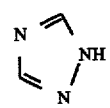

(IV) or a benzotriazole of the formula

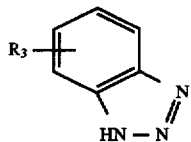 (V)

or mixtures thereof
- (i) with aldehydes $R_1CHO$ or $RCHO$ or mixtures of such aldehydes and diols $HO-R_2-OH$, in which the radicals $R$, $R_1$, $R_2$ and $R_3$ are as defined in claim 1, or
- (ii), if $R_1$ and $R$ are methyl and $R_2$ and $R_3$ are as defined in claim 1, with divinyl ethers of the formula $H_2C=CH-O-R_2-O-CH=CH_2$.

7. A process according to claim 6, wherein mixtures of compounds of the formulae IV and V are employed.

8. A process according to claim 7, wherein the molar ratio IV:V is in the range from 1:9 to 9:1.

9. A process according to claim 7, wherein the molar ratio IV:V is in the range from 1:4 to 4:1.

10. A product or product mixture obtained by the process of claim 6.

11. A composition comprising component A) selected from the group consisting of lubricants, hydraulic fluids metalworking fluids, or coating compositions, and as component B) at least one compound according to claim 1.

12. A composition according to claim 11, wherein the lubricant is an engine oil.

13. A composition according to claim 12, which additionally comprises at least one stabilizer selected from the group consisting of antioxidants, metal deactivators, rust inhibitors, viscosity index improvers, pour-point depressants, dispersants/surfactants, extreme-pressure additives, or antiwear additives.

14. A composition according to claim 13 wherein the antioxidants are selected from the group consisting of phenolic and amine-type antioxidants.

15. A mixture that comprises at least two different compounds of the formula I according to claim 1.

16. A mixture of compounds of the formula I according to claim 19 in which the radicals Y and Z are different with compounds of the formula I in which the radicals Y and Z are identical.

* * * * *